United States Patent
Longo et al.

(10) Patent No.: US 12,029,231 B2
(45) Date of Patent: Jul. 9, 2024

(54) METHOD FOR THE TREATMENT OF DEPRESSION

(71) Applicants: L-NUTRA INC., Los Angeles, CA (US); Daniele La Barbera, Palermo (IT); Giuseppe Maniaci, Palermo (IT); Mario Giuseppe Mirisola, Palermo (IT)

(72) Inventors: Valter Longo, Del Rey, CA (US); Daniele La Barbera, Palermo (IT); Giuseppe Maniaci, Palermo (IT); Mario Giuseppe Mirisola, Palermo (IT)

(73) Assignees: L-NUTRA INC., Los Angeles, CA (US); Daniele La Barbera, Palermo (IT); Giuseppe Maniaci, Palermo (IT); Mario Giuseppe Mirisola, Palermo (IT)

( * ) Notice: Subject to any disclaimer, the term of this patent is extended or adjusted under 35 U.S.C. 154(b) by 152 days.

(21) Appl. No.: 17/373,840

(22) Filed: Jul. 13, 2021

(65) Prior Publication Data

US 2022/0007703 A1    Jan. 13, 2022

Related U.S. Application Data

(60) Provisional application No. 63/050,887, filed on Jul. 13, 2020.

(51) Int. Cl.
| | |
|---|---|
| *A23L 33/125* | (2016.01) |
| *A23L 33/00* | (2016.01) |
| *A23L 33/12* | (2016.01) |
| *A23L 33/18* | (2016.01) |
| *A61K 36/52* | (2006.01) |
| *A61K 36/736* | (2006.01) |
| *A61K 36/889* | (2006.01) |
| *A61K 45/06* | (2006.01) |
| *A61P 25/24* | (2006.01) |

(52) U.S. Cl.
CPC ............... *A23L 33/30* (2016.08); *A23L 33/12* (2016.08); *A23L 33/125* (2016.08); *A23L 33/18* (2016.08); *A61K 36/52* (2013.01); *A61K 36/736* (2013.01); *A61K 36/889* (2013.01); *A61K 45/06* (2013.01); *A61P 25/24* (2018.01)

(58) Field of Classification Search
None
See application file for complete search history.

(56) References Cited

U.S. PATENT DOCUMENTS

| | | | | |
|---|---|---|---|---|
| 2014/0227373 A1* | 8/2014 | Longo | .................. | A61P 3/10 514/274 |
| 2019/0075834 A1* | 3/2019 | Pan | .................. | A23K 50/50 |

FOREIGN PATENT DOCUMENTS

| | | |
|---|---|---|
| WO | 2014137234 A1 | 9/2014 |
| WO | 2015153850 A2 | 10/2015 |

OTHER PUBLICATIONS

Cui et al (J Cell Mol Med 22223-229, published Aug. 7, 2017) (Year: 2017).*
Vandenberghe et al (The Psychological Record 68:231-238, 2018) (Year: 2018).*
Zhou et al (Neurotherapeutics 16:741-760, 2019) (Year: 2019).*
Choi et al (Cell Reports 15:2136-2146, 2016) (Year: 2016).*
Incredible Health Center website (available online at https://www.incrediblehealthcenter.com/is-prolon-right-for-you/; accessed Feb. 20, 2024) (Year: 2024).*
Hussin N.M. et al., "Efficacy of fasting and calorie restriction (FCR) on mood and depression among ageing men", The Journal of Nutrition, Health & Aging, vol. 17, No. 8, 2013, pp. 674-680.
Lassale C. et al., "Healthy dietary indices and risk of depressive outcomes: a systematic review and meta-analysis of observation studies", Molecular Psychiatry, vol. 24, No. 7, 2019, pp. 965-986.
Maniaci G. et al., "Efficacy of a fasting-mimicking diet in functional therapy for depression: A randomised controlled pilot trial", Journal of Clinical Psychology, vol. 76, No. 10, May 11, 2020, pp. 1807-1817.
Search Report of Italian Application No. IT20200016957 dated Mar. 29, 2021.

* cited by examiner

*Primary Examiner* — Craig D Ricci
(74) *Attorney, Agent, or Firm* — Silvia Salvadori, P.C.; Silvia Salvadori

(57) ABSTRACT

A method for treating depression in a human subject, which comprises administering for a first time period a fasting mimicking diet (FMD) component providing less than 50% of the normal calorie intake of the subject with both protein restriction and sugar restriction; and administering for a second time period a re-feeding diet component that provides 60-100% of the normal calorie intake of the subject; the fasting mimicking diet component and the re-feeding diet component are administered for multiple cycles, and the subject undergoes a psychotherapeutic treatment for the whole duration of the multiple cycles.

14 Claims, 1 Drawing Sheet

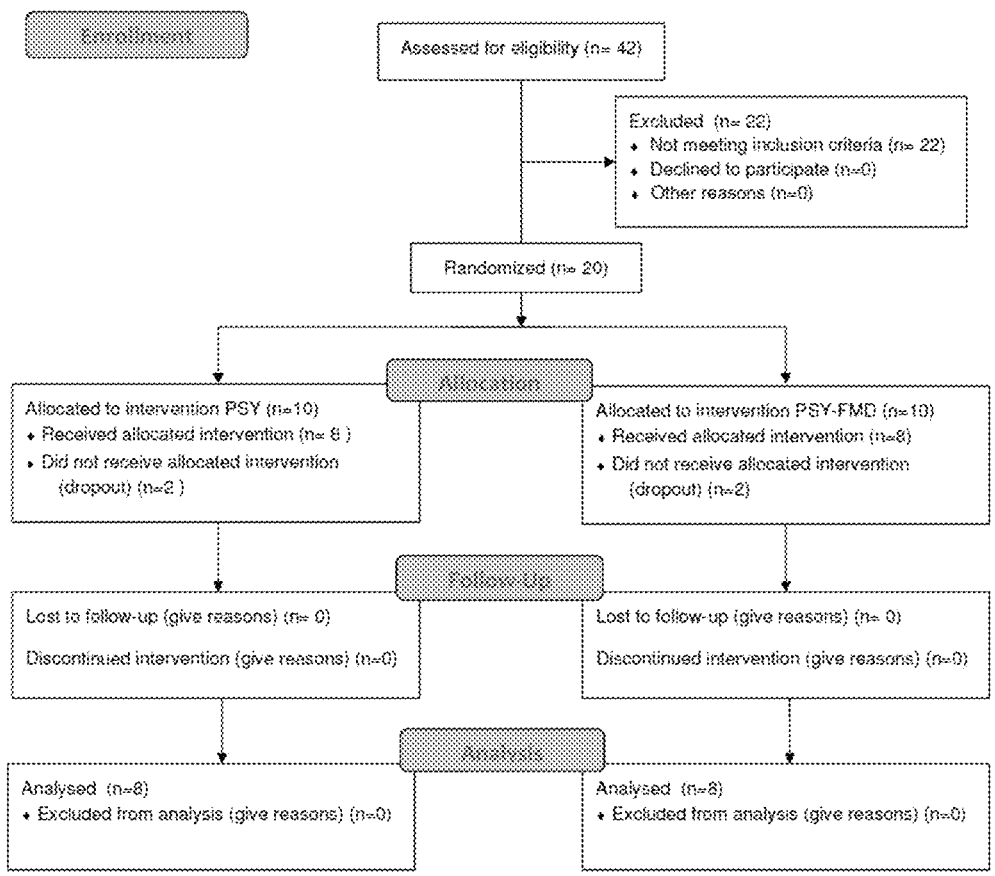

METHOD FOR THE TREATMENT OF DEPRESSION

This application claims priority to and the benefit of U.S. Provisional Patent Application No. 63/050,887 filed on Jul. 13, 2020, the content of which is all incorporated herein by reference in its entirety.

The article of Maniaci et al. "Efficacy of a fasting-mimicking diet in functional therapy for depression: A randomized controlled pilot trial" (J. Clin. Psychol 2020; 76:1807-1817) is inventors' own work (37 C.F.R. § 1.77(b)(6)).

TECHNICAL FIELD

The present invention relates to the technical field of the pharmaceutical and dietary industries.

In particular, the invention refers to a method for the treatment of depression in a human subject.

PRIOR ART

Depression, which affects 4.4% of the world's population (World Health Organization, 2017), is a systemic disorder recognized as a leading cause of illness and disability worldwide. Depression raises the risk of several disorders (Sotelo & Nemeroff, 2017), partly due to its association with inflammation (Halaris, 2019) and potential to be influenced by changes in microbiota (Winter, Hart, Charlesworth, & Sharpley, 2018). Current research suggests that depression is caused by a combination of genetic (Dunn et al., 2015), environmental (Gotlib, Goodman, & Humphreys, 2020), and psychological factors (Hammen, 2018), including child abuse (Infurna et al., 2016), stressful life events (Berg, Rostila, & Hjern, 2016), and low self-esteem (Shah et al., 2020). Indeed, recent findings showing that individuals with high self-esteem reported a lower risk for developing depression support the vulnerability model of low self-esteem and depression (Orth, Robins, Meier, & Conger, 2016).

To date, psychotherapy programs shown to be effective in treating depression include cognitive-behavioral therapy (Grosse Holtforth et al., 2019), psychodynamic (de Roten et al., 2017), and mind-body approaches (e.g., Chan et al., 2016). Empirical evidence also suggests that functional therapy, by direct intervening in the mind-body system, can induce changes in an individual's cognitive, emotional, and psychological systems (Maniaci et al., 2018; Perciavalle et al., 2017). For depression, the purpose of functional therapy is to increase mood and self-esteem via several bodily, cognitive, and emotional techniques geared toward helping patients to improve the basic experiences of the self that are altered by the disorder (for an explanation of functional theory, see Rispoli, 2016; Dipasquale, Magnano, Blandini, Gueli, & Fecarotta, 2019).

A considerable body of literature highlights the role of a healthy diet in reducing the risk of depression (Lassale et al., 2019). By contrast, eating according to Western dietary patterns has been associated with depressed mood (Masana et al., 2018). Indeed, the typology of diet modulates several key biological processes, including inflammation, involved in mood disorders (Halaris, 2019).

A specific typology of diet that includes fasting has been shown to affect several health-related parameters, including stress resistance, self-renewal, and lineage-balanced regeneration (de Braud et al., 2018), as well as to reduce immunosuppression and mortality caused by chemotherapy in mice (Cheng et al., 2014). It also promoted hippocampal neurogenesis and improved cognitive performance and motor coordination (Brandhorst et al., 2015). Currently, several ongoing clinical trials are evaluating the effects of fasting mimicking diets (FMD) in cancer patients (de Braud et al., 2018; Vernieri et al., 2019) and in the treatment of type 2 diabetes (e.g., ClinicalTrials.gov NCT03811587).

However, though the association between diet and depression is fairly certain, to the Applicants' knowledge no studies have investigated the effects of a fasting mimicking diet protocol on depression and no reliable predictions on the effects that FMD may have in the treatment of depression can be made.

For these reasons, the research carried out by the Applicants focused on the study of the possible favorable effect of FMD in the treatment of depression.

Given those premises, the Applicants envisaged conducting a clinical trial having two aims: (a) to verify the efficacy of a structured functional therapy program delivered in individual sessions for patients with depression and (b) to determine whether the integration of a fasting-mimicking diet protocol into the structured functional therapy program can significantly improve clinical outcomes.

The present invention is the result of the above research activity.

SUMMARY OF THE INVENTION

In one aspect, the present invention refers to a method for treating depression in a human subject, the method comprising:
administering a fasting mimicking diet (FMD) component for a first time period, said fasting mimicking diet component providing less than 50% of the normal calorie intake of the subject with both protein restriction and sugar restriction; and
administering a re-feeding diet component for a second time period, said re-feeding diet component providing 60-100% of the normal calorie intake of the subject;
wherein the fasting mimicking diet component and the re-feeding diet component are administered for multiple cycles, and
wherein said subject undergoes a psychotherapeutic treatment for the whole duration of said multiple cycles.

The normal calorie intake of the subject is the number of kcal that the subject consumes in order to maintain its weight. The normal calorie intake of the subject can be estimated by interviewing the subject or by considering the subject weight. As a rough guide, the normal calorie intake of the subject is on average 2000-3000 kcal/day for men and 1600-2400 kcal/day for women.

Preferably, the first time period is from 2 to 10 days and the second time period is from 7 to 85 days.

More preferably, the first time period is from 2 to 6 days, particularly 5 days, and the second time period is 25-26 days.

Preferably, said multiple cycles are 2 to 5 cycles, more preferably 3 cycles.

Examples of FMD protocols that can be used in the present invention are found in patent applications U.S. Ser. Nos. 12/430,058 and 13/488,590.

The fasting mimicking diet component provides the subject preferably with no more than 1160 kcal/day, and in particular, no more than 800 kcal/day.

In one embodiment, the fasting mimicking diet component provides the subject with 100 to 1000 kcal/day.

The fasting mimicking diet component provides the subject, with 1000, 957, 700, 500, 300, or 100 kcal/day, in ascending order of preference.

In one embodiment, the fasting mimicking diet component provides the subject with a protein amount less than or equal to 36 g/day. In particular, the fasting mimicking diet component provides the subject with a protein amount equal to 36, 20, 10, or 5 or 0 g/day, in increasing order of preference.

If carbohydrates are present in the fasting mimicking diet component, they provide no more than half of the calories provided by the aforementioned diet component.

Preferably the fasting mimicking diet component provides the subject with no more than no more than 11 kcal/kg of body weight/day (in particular no more than 8, 5, or 2 kcal) and no more than 0.4 g proteins/kg of body weight/day (in particular no more than 0.3, 0.2 or 0.1 g).

Other examples of FMD can be found in the WO 2014/066426 and WO 2014/127000 applications.

Lists of nutrients contained in the fasting mimicking diet component referring to a 80-90 kg subject, are shown in Tables 1-2 below.

TABLE 1

|  | Day 1 | Days 2, 3, 4, 5 |
|---|---|---|
| Total calories | 1152 | 809 |
| Fats | 56% | 46% |
| Carbohydrates | 34% | 46% |
| of which sugars | 10% | 9% |
| Protein | 10% | 9% |

TABLE 2

|  | Unit | Day 1 | % DD | Days 2, 3, 4, 5 | % DD | mean % DD |
|---|---|---|---|---|---|---|
| Protein | g | 29 |  | 18 |  |  |
| Fats | g | 72 |  | 41 |  |  |
| Carbohydrates (by difference) | g | 98 |  | 91 |  |  |
| From sugars | g | 29 |  | 17.6 |  |  |
| Dietary fiber | g | 22 | 86 | 14 | 56 | 62 |
| Calcium | mg | 604 | 60 | 426 | 43 | 46 |
| Iron | mg | 13 | 77 | 10 | 55 | 60 |
| Magnesium | mg | 387 | 97 | 230 | 58 | 65 |
| Phosphorus | mg | 390 | 39 | 276 | 28 | 30 |
| Potassium | mg | 2519 | 72 | 1795 | 51 | 55 |
| Sodium | mg | 2427 | 101 | 1750 | 73 | 79 |
| Zinc | mg | 7 | 46 | 4.2 | 28 | 32 |
| Copper | mg | 1.5 | 76 | 1.2 | 59 | 63 |
| Manganese | mg | 3 | 148 | 1.9 | 95 | 105 |
| Selenium | mg | 7 | 10 | 5.3 | 8 | 8 |
| Vit. A | IU | 39254 | 785 | 27549 | 551 | 598 |
| Vit. C | mcg | 236 | 393 | 138 | 229 | 261 |
| Vit. B1 | mg | 4 | 209 | 2.2 | 113 | 132 |
| Vit. B2 | mg | 3.8 | 191 | 2 | 109 | 126 |
| Vit. B3 (niacin) | mg | 28.5 | 143 | 18 | 92 | 102 |
| Vit. B5 (pantothenic acid) | mg | 1.2 | 12 | 1.0 | 10 | 10 |
| Vit. B6 | mg | 4.0 | 200 | 2.2 | 111 | 129 |
| Vit. B9 (folate) | mg | 479 | 120 | 317 | 79 | 87 |
| Vit. B12 | mcg | 16 | 227 | 16 | 227 | 227 |
| Vit. D | IU | 952 | 238 | 952 | 238 | 238 |
| Vit. E | mcg | 25 | 127 | 16 | 80 | 89 |
| Vit. K | mg | 1795 | 2243 | 1110 | 1387 | 1559 |

DD = Daily dose

Typically, in the FMD protocol the usual diet of the subjects is substituted for a predefined number of days (e.g. 5 days), in which the subject drinks plenty of water. For normal weight subjects (Body Mass Index between 18.5 and 25), the fasting mimicking diet component is taken up once a month (preferably for 5 days) while for the next 25-26 days the subject receives the re-feeding diet component.

This is for the first 3 months; subsequently the subject receives the fasting mimicking diet component for 5 days and the re-feeding diet component for about 85 days continuing with a 5-day cycle of fasting mimicking diet component followed by 85 days of re-feeding diet component. The subject weight is monitored so that the subject reacquires at least 95% of the weight lost during the administration of the fasting mimicking diet component, before starting the new cycle (for normal weight subjects). In overweight subjects, a weight loss following FMD cycles is admissible as long as it is well tolerated and the weight of the subject does not drop below the normal BMI range.

Preferably, the fasting mimicking diet component comprises proteins in an amount that is less than 15% of the total calories provided by the fasting mimicking diet component.

Preferably, the fasting mimicking diet component comprises sugars in an amount that is less than 15% of the total calories provided by the fasting mimicking diet component.

Preferably, the fasting mimicking diet component provides the subject with 9 to 15 kcal/kg of body weight/day on day 1, and 6 to 10 kcal/kg of body weight/day on days 2 to 5.

Most preferably, the fasting mimicking diet component provides the subject with 6 to 12 kcal/kg/body weight/day on day 1, and 4 to 8 kcal/kg/body weight/day on day 2 to 5.

Advantageously, the fasting mimicking diet component provides the subject with 15 kcal/kg/body weight/day on day 1, and 8 kcal/kg/body weight/day on day 2 to 5.

Preferably, the fasting mimicking diet component comprises at least 60% calories from fatty acids, 2-5% calories from glycerol and up to 5% calories from plant-based proteins and a maximum of 35% calories from carbohydrates.

Preferably, said fasting mimicking diet component comprises complex carbohydrates from plant sources, which preferably comprise soy, rice or other cereals.

Preferably at least 50% of the calories from fatty acids are from coconut oil and tree nuts. The latter preferably comprise walnuts, macadamia nuts and/or almonds.

Then the subject is fed with food with a high content of monounsaturated and polyunsaturated fats and a reduced content of proteins and sugars (≥40% calories coming from fat). This is because a diet based on these foods has beneficial effects that are similar to those of fasting [13].

The refeeding diet component can also consist in the usual diet followed by the subject, provided that such diet provides the subject with a number of Kcal/day that does not exceed his/her normal calorie intake as defined above.

The present invention will be further described with reference to a randomized controlled trial (RCT) that has been performed to compare the effects of psychotherapy, in particular functional therapy, versus psychotherapy (functional therapy) along with a fasting-mimicking diet among patients with depression. This trial was conducted in the outpatient clinic of the Psychiatry Section of the Department of Biomedicine, Neuroscience and Advanced Diagnostics at the University of Palermo.

BRIEF DESCRIPTION OF THE DRAWINGS

FIG. 1 is a flow chart illustrating the steps of the above-mentioned randomized controlled trial.

DETAILED DESCRIPTION

The above mentioned randomized controlled trial had two main aims: (a) to verify the efficacy of a structured functional therapy program delivered in individual sessions for patients with depression and (b) to determine whether the integration of a fasting-mimicking diet protocol into the structured functional therapy program can significantly improve clinical outcomes.

Patients could volunteer to enroll in the study during a 9-month period from September 2018 to May 2019. All volunteers were subjected to structured telephone screening to determine their eligibility in terms of the following inclusion and exclusion criteria: aged from 18 to 60 years old, seeking treatment for mood problems, not receiving any concurrent treatment, not receiving any psychopharmacological treatment for depression in the previous 12 months, and not practicing yoga or meditation. Patients with past or current drug abuse or addiction (excluding nicotine), chronic inflammation disease, severe hepatic failure, serious infection (e.g., hepatitis B), cancer in the previous 6 months or regular use of anti-inflammatory drugs for more than 15 days per month were also excluded.

To further examine other eligibility criteria and depression, consultations with a clinical psychologist and psychiatrist were organized together with the administration of the psychological tests. To qualify to participate in the RCT, patients had to score more than 13 points on the Beck Depression Inventory-II (BDI-II) and report a body mass index (BMI) between 18.5 and 30.0 at the initial assessment. The exclusion criteria were an intelligence quotient (IQ) less than 65, active suicidal ideation with a plan, and a current or lifetime diagnosis of any psychotic disorder, eating disorder, bipolar disorder, primary anxiety disorder, or a borderline, schizotypal, or antisocial personality disorder.

To assign participants into the study's groups, a randomization sequence was created using an online randomization service (www.randomization.com). Participants were randomized into either an experimental group or a control group via block randomization, with 5 blocks of size 4, such that participants in the groups were evenly distributed among the therapists.

Afterwards, all subjects received consultation by a nutritionist, who prescribed the fasting-mimicking diet to the experimental group, whereas those in the control group were asked to maintain their usual diets and to not make any dietary changes, which they monitored by reporting all food and beverages consumed in a food diary. Last, all participants received the functional therapy protocol. All measures were administered at baseline, at the end of treatment (i.e., 3 months after baseline), and at follow-up (i.e., 6 months after baseline).

Measures

Screening Measures

To verify the absence of exclusion criteria, an ad hoc sociodemographic questionnaire, a shortened and well-validated version of the Wechsler Adult Intelligence Scale—Revised (Velthorst et al., 2013), and the Italian version of the Millon Clinical Multiaxial Inventory-III ($\alpha=0.65$-$0.80$, $r=0.76$-$0.93$; Zennaro, Ferracuti, Lang, & Sanavio, 2008) were used to assess sociodemographic variables (e.g., age, sex, marital status, and occupation), IQ, and personality disorders and primary psychiatric disorders, respectively.

Outcome Measures

The primary outcome measure was the Italian version of the BDI-II, used to assess the severity of depressive symptoms (Ghisi, Flebus, Montano, Sanavio, & Sica, 2006). The test has shown good psychometric properties ($\alpha=0.80$-$0.87$, $r=0.76$; Sica & Ghisi, 2007). The secondary outcome measures were the Basic Self-Esteem Scale (Forsman, Johnson, Ugolini, Bruzzi, & Raboni, 2003), used to assess self-esteem, and the brief Italian version of the World Health Organization Quality of Life (WHOQOL-BREF) instrument (De Girolamo et al., 2000), used to assess subjective perception of quality of life. The Italian Basic Self-Esteem Scale has shown good psychometric properties ($\alpha=0.85$, $r=0.81$-$0.83$; Forsman et al., 2003), as has the WHOQOL-BREF ($\alpha=0.65$-$0.80$, $r=0.76$-$0.93$; De Girolamo et al., 2000).

At the end of the psychological assessment, anthropometric parameters (i.e., weight, height, and waist circumference) were measured, after which patients received a consultation with a nutritionist.

Intervention

Five therapists with 4-year postgraduate training in functional therapy implemented the intervention after receiving refresher training in the application of the structured functional therapy protocol for depression. From a senior clinical psychologist with specialist training in functional therapy, they also received weekly clinical supervision focused on maintaining fidelity to the manualized intervention. Each therapist treated four patients.

A nutritionist prescribed the fasting-mimicking diet protocol following consultation with each patient. After the assessment, each eligible patient was randomized to receive either functional therapy with the fasting-mimicking diet or functional therapy only and assigned to the next available therapist on the intervention schedule. As it can be seen from the flow chart of FIG. 1, although 42 consecutive treatment-seeking patients were screened, four were excluded due to psychotic symptoms and another 18 due to meeting other exclusion criteria. The resulting sample comprised 20 participants with depression, four of whom dropped out after attending an average of 4.6 (SD=1.86) treatment sessions.

Treatments

Experimental Group

During a 3-month period, participants randomized into the experimental group were administered the functional therapy protocol over the course of 20 individual sessions, scheduled to occur twice weekly for the first 2 months and once weekly for the last month. The treatment program was customized to treat depression by increasing mood, self-esteem, and quality of life (Rispoli, 2008). More precisely, the program was geared toward reducing or eliminating mood imbalances through several bodily, cognitive, and emotional techniques (e.g., deep breathing and specific guided imagery), as well as techniques to improve assertiveness and social abilities.

Participants in the experimental group also followed a fasting-mimicking diet protocol developed by Wei et al. (2017) consisting of three 5-day cycles per month. On Day 1, the fasting-mimicking diet prescribed 1,090 kcal (i.e., 10% protein, 56% fat, and 34% carbohydrates); on Days 2-5, that formulation was proportionally reduced to 725 kcal (i.e., 9-10% protein, 44-56% fat, and 34-47% carbohydrates). Between the cycles, participants were not subject to any study-imposed dietary restrictions. Once treatment ended, all participants again completed the assessment administered prior to treatment in order to analyze their achievement of the expected outcomes. They completed the same assessment one more time 3 months after treatment had ended.

Control Group

Participants randomized into the control group completed the same functional therapy program administered in the experimental group but did not follow the fasting-mimicking diet protocol. As a control condition, at the end of their nutrition consultation, the nutritionist advised them to keep a food diary, and they were instructed to continue their usual daily diets. If they had any doubts or questions, then they were free to send an email to the nutritionist.

Statistical Analysis

Group-based differences in demographic features and pre-treatment measures were analyzed with $\chi^2$ tests or Fisher's exact tests. The Friedman test was used to evaluate any statistically significant difference on depression, self-esteem, and quality of life, within the groups at baseline, after treatment, and follow-up. In case of a significant value, the Wilcoxon signed-rank test was performed in order to evaluate which time points were significantly different from one another. Last, the Mann-Whitney test was performed to analyze differences between groups before and at each time point during the study. All statistical analyses were performed in the Statistical Package for the Social Sciences for Windows 22.0 and assumed an alpha risk of 5%.

Results

Baseline Data

No significant differences between groups emerged in the sociodemographic characteristics of age (Mann-Whitney U=48.500, z=−0.114, p=0.912); gender, p=0.650; marital status, p=1.000; or level of education, $\chi^2$ (3)=2.778, p=0.427. Both groups were also homogeneous in terms of the primary and secondary outcome measures of depressive symptoms, (Mann-Whitney U=45.500, z=−0.341, p=0.739); self-esteem level, (Mann-Whitney U=29.500, z=−1.661, p=0.123); and quality of life, in terms of physical health (Mann-Whitney U=33.000, z=−1.298, p=0.218); psychological health (Mann-Whitney U=46.000, z=−0.307, p=0.796); social relationships (Mann-Whitney U=46.000, standardized test statistic=−0.308, p=0.796); and environmental health (Mann-Whitney U=48.000, z=−0.152, p=0.912). Baseline BMI between the groups did not significantly differ, either (Mann-Whitney U=28.000, z=−1.663, p=0.105).

Outcomes and Estimation

Within-Group Differences (a) Control Group: A Friedman test was conducted and it showed a significant difference after treatment on depression levels $\chi^2$ (2)=12.452, p=0.001; levels of self-esteem $\chi^2$ (2)=6.333, p=0.049; physical quality of life $\chi^2$ (2)=7.770, p=0.015; and social relationships quality of life $\chi^2$ (2)=8.087, p=0.010. Post-hoc tests using a Wilcoxon signed-rank test revealed a significant main effect of time after treatment (T0-T1), meaning that functional therapy led to significantly reduced levels of depression (z=−2.527, p=0.012), together with increased levels of self-esteem (z=−2.121, p=0.034); physical (z=−2.527, p=0.012) and social relationships quality of life (z=−2.401, p=0.016). At follow-up, the Wilcoxon test demonstrated that there was no significant difference 3 months after the control group received the treatment.

(b) Intervention Group: A Friedman test showed a significant difference after treatment on depression levels $\chi^2$ (2)=14.800, p=0.00005; levels of self-esteem $\chi^2$ (2)=16.800, p=0.000; and all dimensions of quality of life, such as physical $\chi^2$ (2)=10.889, p=0.003; psychological $\chi^2$ (2)=14.727, p=0.000; social relationships $\chi^2$ (2)=11.879, p=0.001; environmental $\chi^2$ (2)=13.556, p=0.0003. Furthermore, a statistically significant difference on BMI was found $\chi^2$ (2)=13.556, p=0.0003. The results of the Wilcoxon test indicated a significant main effect of time after treatment (T0-T1) for depression levels (z=−2.668, p=0.008), levels of self-esteem (z=−2.716, p=0.007), all dimensions of quality of life, such as physical (z=−2.547, p=0.011), psychological (z=−2.668, p=0.008), social relationships (z=−2.521, p=0.012), and environmental (z=−2.666, p=0.008); and BMI (z=−2.666, p=0.008). As well as in the control group, the Wilcoxon test demonstrated that there was no significant difference 3 months after the experimental group received the treatment.

Between-Group Differences

A Mann-Whitney test indicated that the increase of self-esteem at the end of the treatment was significantly greater for the experimental group (Mdn=75.000) than for the control group (Mdn=25.000), U=6.500, z=−2.949, p=0.002; r=−0.715. A significant increase of psychological quality of life was highlighted in the experimental group (Mdn=27.085) compared to the control group (Mdn=12.500), U=11.000, z=−2.210, p=0.027; r=−0.375. Furthermore, significant differences between groups were highlighted regarding the decrease of BMI (U=10.000, z=−2.276, p=0.02; r=−0.569), with greater change in the experimental group (Mdn=−1.8) than in the control group (Mdn=−0.05). No significant differences from T1 to T2 were found. Moreover, a Mann-Whitney test indicated that there were no significant differences between groups (pretreatment and posttreatment) in depression levels (U=27.000; z=−0.868; p=0.204), and physical (U=25.000; z=−1.060; p=0.309), social relationships (U=33.500; z=−0.245; p=0.840) and environmental (U=33.000; z=−0.290, p=0.796) quality of life.

Discussion

This RCT was designed to evaluate the efficacy of a fasting-mimicking diet protocol integrated into a structured functional therapy program for patients with depression in terms of its effects on their depressive symptoms, self-esteem, and quality of life. Among our results, depressive symptoms significantly decreased in both groups, although more, but not significantly more, for patients in the experimental group than in the control group. Furthermore, from post-treatment to the 3-month follow-up, no significant worsening surfaced in any outcome measures in both groups, which implies that improvements had been maintained. Beyond that, a reduction in mean BMI in the experimental group only suggests good compliance with the fasting-mimicking diet prescribed and general health benefits, because no patients showed a BMI below the normal level.

The fasting-mimicking diet combined with functional therapy significantly improved the self-esteem and quality of life of patients with depression.

Among other findings, functional therapy combined with the fasting-mimicking diet was significantly more effective than functional therapy alone in improving self-esteem and several dimensions of quality of life. It is possible that practicing a healthy diet can improve patients' quality of life, because they can gain a sense of their full strength as well as their capacity to manage and enjoy their everyday lives. Moreover, patients randomized to complete the functional therapy-fasting-mimicking diet program demonstrated good compliance and rarely dropped out, which aligns with reported dropout rates of approximately 20% in recent similar studies (Cooper & Conklin, 2015; Zilcha-Mano et al., 2016).

Such findings suggest the usefulness of working through depression by following an integrated approach that involves food as a medicine for improving the outcomes of psychotherapy. In fact, because of the connections between the central nervous system and the immune system via the hypothalamic-pituitary-adrenal axis, a disruption of one can disrupt the other and cause low-grade systemic inflammation (Halaris, 2019).

Although it may be difficult for patients with depression to adopt radical and chronic dietary changes, a periodic fasting-mimicking diet undertaken for only 5 days per month could prove to be more feasible and effective than other diet protocols. Not only would that arrangement allow patients with depression to continue observing a diet that they enjoy for the remaining 25 days each month, but it would also slowly improve their everyday diets based on the effects of a periodic fasting-mimicking diet.

REFERENCES

Berg, L., Rostila, M., & Hjern, A. (2016). Parental death during childhood and depression in young adults—A national cohort study. *Journal of Child Psychology and Psychiatry and Allied Disciplines*, 57, 1092-1098. https://doi.org/10.1111/jcpp. 12560

Brandhorst, S., Choi, I. Y., Wei, M., Cheng, C. W., Sedrakyan, S., Navarrete, G., . . . Longo, V. D. (2015). A periodic diet that mimics fasting promotes multi-system regeneration, enhanced cognitive performance, and healthspan. *Cell Metabolism*, 22, 86-99. https://doi.org/10.1016/j.cmet.2015.05.012

Chan, C. H. Y., Ji, X. W., Chan, J. S. M., Lau, B. H. P., So, K. F., Li, A., . . . Chan, C. L. W. (2016). Effects of the integrative mind-body intervention on depression, sleep disturbances and plasma IL-6. *Psychotherapy and Psychosomatics*, 86, 54-56. https://doi.org/10.1159/000447541

Cheng, C. W., Adams, G. B., Perin, L., Wei, M., Zhou, X., Lam, B. S., . . . Longo, V. D. (2014). Prolonged fasting reduces IGF-1/PKA to promote hematopoietic-stem-cell-based regeneration and reverse immunosuppression. *Cell Stem Cell*, 14, 810-823. https://doi.org/10.1016/j.stem.2014.04.014.

Cooper, A. A., & Conklin, L. R. (2015). Dropout from individual psychotherapy for major depression: A meta-analysis of randomized clinical trials. *Clinical Psychology Review*, 40, 57-65. https://doi.org/10.1016/j.cpr.2015.05.001

De Braud, F. G., Milano, M., Fucà, G., Mariani, G., Capri, G., Bianchi, G. V., . . . Vernieri, C. (2018). Safety and metabolic effects of cyclic fasting mimicking diet (FMD) in cancer patients. *Journal of Clinical Oncology*, 36, e14549. https://doi.org/10.1200/jco.2018.36.15_suppl.e14549.

De Girolamo, G. D., Rucci, P., Scocco, P., Becchi, A., Coppa, F., D'Addario, A., . . . Soldani, L. (2000). Quality of life assessment: Validation of the Italian version of the WHOQOL-Brief—La valutazione della qualita della vita: Validazione del WHOQOL-Breve. *Epidemiologia e Psichiatria Sociale*, 9, 45-55.

deRoten, Y., Ambresin, G., Herrera, F., Fassassi, S., Fournier, N., Preisig, M., & Despland, J. N. (2017). Efficacy of an adjunctive brief psychodynamic psychotherapy to usual inpatient treatment of depression: Results of a randomized controlled trial. *Journal of Affective Disorders*, 209, 105-113. https://doi.org/10.1016/j.jad.2016.11.013.

Dipasquale, F., Magnano, P., Blandini, M., Gueli, R., & Fecarotta, P. (2019). A prototype scale for the validation of the Neo-Functionalism theoretical model in psychology: The Basic Experience of the Self's Assessment Form. *Life Span and Disability*, 1, 77-93.

Dunn, E. C., Brown, R. C., Dai, Y., Rosand, J., Nugent, N. R., Amstadter, A. B., & Smoller, J. W. (2015). Genetic determinants of depression: Recent findings and future directions. *Harvard Review of Psychiatry*, 23, 1-18. https://doi.org/10.1097/HRP.0000000000000054

Field, A. (2013). *Discovering statistics using IBM SPSS statistics*. London: Sage.

Forsman, L., Johnson, M., Ugolini, V., Bruzzi, D., & Raboni, D. (2003). *Basic SE. Basic Self-Esteem Scale. Valutazione dell'autostima di base negli adulti. Con protocolli*. Trento: Erickson.

Ghisi, M., Flebus, G. B., Montano, A., Sanavio, E., & Sica, C. (2006). *BDI-II. Beck Depression Inventory II. Manuale*. Florence: Giunti O.S.

Gotlib, I. H., Goodman, S. H., & Humphreys, K. L. (2020). Studying the intergenerational transmission of risk for depression: Current status and future directions. *Current Directions in Psychological Science*, 29, 1-6. https://doi.org/10.1177/0963721420901590.

Grosse Holtforth, M., Krieger, T., Zimmermann, J., Altenstein-Yamanaka, D., Dörig, N., Meisch, L., & Hayes, A. M. (2019). A randomized-controlled trial of cognitive-behavioral therapy for depression with integrated techniques from emotion-focused and exposure therapies. *Psychotherapy Research*, 29, 30-44. https://doi.org/10.1080/10503307.2017.1397796

Halaris, A. (2019). Inflammation and depression but where does the inflammation come from? *Current Opinion in Psychiatry*, 32, 422-428. https://doi.org/10.1097/YC0.0000000000000531.

Hammen, C. (2018). Risk factors for depression: An autobiographical review. *Annual Review of Clinical Psychology*, 14, 1-28. https://doi.org/10.1146/annurev-clinpsy-050817-084811.

Infurna, M. R., Reichl, C., Parzer, P., Schimmenti, A., Bifulco, A., & Kaess, M. (2016). Associations between depression and specific childhood experiences of abuse and neglect: A meta-analysis. *Journal of Affective Disorders*, 190, 47-55. https://doi.org/10.1016/j.jad.2015.09.006.

Knox, E., & Muros, J. J. (2017). Association of lifestyle behaviours with self-esteem through health-related quality of life in Spanish adolescents. *European Journal of Pediatrics*, 176, 621-628. https://doi.org/10.1007/s00431-017-2886-z.

Lassale, C., Batty, G. D., Baghdadli, A., Jacka, F., Sánchez-Villegas, A., Kivimäki, M., & Akbaraly, T. (2019). Healthy dietary indices and risk of depressive outcomes: A systematic review and meta-analysis of observational studies. *Molecular Psychiatry*, 24, 965-986. https://doi.org/10.1038/s41380-018-0237-8.

Maniaci, G., La Cascia, C., Ferraro, L., Picone, F., Sideli, L., Seminerio, F., . . . Cannizzaro, C. (2018). The efficacy of a functional therapy program for gambling disorder: A Pilot study. *Acta Medica Mediterranea*, 34, 1447-1452. https://doi.org/10.19193/0393-6384_2018_5_220

Masana, M. F., Haro, J. M., Mariolis, A., Piscopo, S., Valacchi, G., Bountziouka, V., . . . Panagiotakos, D. B. (2018). Mediterranean diet and depression among older individuals: The multinational MEDIS study. *Experimental Gerontology*, 110, 67-72. https://doi.org/10.1016/j.exger.2018.05.012.

Orth, U., Robins, R. W., Meier, L. L., & Conger, R. D. (2016). Refining the vulnerability model of low self-esteem and depression: Disentangling the effects of genuine self-esteem and narcissism. *Journal of Personality and Social Psychology*, 110, 133-149. https://doi.org/10.1037/pspp0000038.

Parletta, N., Zarnowiecki, D., Cho, J., Wilson, A., Bogomolova, S., Villani, A., . . . O'Dea, K. (2019). A Mediterranean-style dietary intervention supplemented with fish oil improves diet quality and mental health in people with depression: A randomized controlled trial (HELFIMED). *Nutritional Neuroscience*, 22, 474-487. https://doi.org/10.1080/1028415X.2017.1411320.

Perciavalle, V., Blandini, M., Fecarotta, P., Buscemi, A., Di Corrado, D., Bertolo, L., . . . Coco, M. (2017). The role of deep breathing on stress. *Neurological ScienceS*, 38, 451-458. https://doi.org/10.1007/s10072-016-2790-8.

Rispoli, L. (2008). *The Basic Experiences and the Development of the Self Development from the point of view of Functional Psychotherapy*. Frankfurt: Peter Lang.

Rispoli, L. (2016). *Il corpo in psicoterapia oggi. Neo-Funzionalismo e Sistemi integrati*. Milan: Franco Angeli.

Sánchez-Villegas, A., Cabrera-Suárez, B., Molero, P., González-Pinto, A., Chiclana-Actis, C., Cabrera, C., . . . Hernández-Fleta, J. L. (2019). Preventing the recurrence of depression with a Mediterranean diet supplemented with extra-virgin olive oil. the PREDI-DEP trial: Study protocol. *BMC Psychiatry*, 19, 63. https://doi.org/10.1186/s12888-019-2036-4

Shah, S. M., Al Dhaheri, F., Albanna, A., Al Jaberi, N., Al Eissaee, S., Alshehhi, N. A., . . . Betancourt, T. S. (2020). Self-esteem and other risk factors for depressive symptoms among adolescents in United Arab Emirates. *PLoS One*, 15, e0227483. https://doi.org/10.1371/journal.pone.0227483

Sica, C., & Ghisi, M. (2007). The Italian versions of the Beck Anxiety Inventory and the Beck Depression Inventory-II: Psychometric properties and discriminant power. In M. A. Lange (Ed.), *Leading-Edge Psychological Tests and Testing Research* (pp. 27-50). Hauppauge, N.Y.: NOVA Science.

Simeone, T. A., Simeone, K. A., & Rho, J. M. (2017). Ketone bodies as anti-seizure agents. *Neurochemical Research*, 42, 2011-2018. https://doi.org/10.1007/s11064-017-2253-5.

Sotelo, J. L., & Nemeroff, C. B. (2017). Depression as a systematic disease. *Personalized Medicine in Psychiatry*, 1, 11-25. https://doi.org/10.1016/j.pmip.2016.11.002.

Velthorst, E., Levine, S. Z., Henquet, C., De Haan, L., Van Os, J., Myin-Germeys, I., & Reichenberg, A. (2013). To cut a short test even shorter: Reliability and validity of a brief assessment of intellectual ability in Schizophrenia—A control-case family study. *Cognitive Neuropsychiatry*, 18, 574-593. https://doi.org/10.1080/13546805.2012.731390.

Vernieri, C., Signorelli, D., Galli, G., Ganzinelli, M., Moro, M., Fabbri, A., . . . Garassino, M. C. (2019). Exploiting fasting-mimicking diet and metformin to improve the efficacy of platinum-pemetrexed chemotherapy in advanced LKB1-inactivated lung adenocarcinoma: The FAME trial. *Clinical Lung Cancer*, 20, e413-e417. https://doi.org/10.1016/j.cllc.2018.12.011.

Wei, M., Brandhorst, S., Shelehchi, M., Mirzaei, H., Cheng, C. W., Budniak, J., . . . Longo, V. D. (2017). Fasting-mimicking diet and markers/risk factors for aging, diabetes, cancer, and cardiovascular disease. *Science Translational Medicine*, 9, eaai8700. https://doi.org/10.1126/scitranslmed.aai8700.

Winter, G., Hart, R. A., Charlesworth, R. P. G., & Sharpley, C. F. (2018). Gut microbiome and depression: What we know and what we need to know. *Reviews in the Neurosciences*, 29, 629-643. https://doi.org/10.1515/revneuro-2017-0072.

World Health Organization. (2017). *Depression and other common mental disorders: Global health estimates*. Retrieved from http://apps.who.int/iris/bitstream/handle/10665/254610/WHO-MSD-MER-2017.2-eng.pdf Zennaro, A., Ferracuti, S., Lang, M., & Sanavio, E. (2008). *MCMI-III. Millon Clinical Multiaxial Inventory—III. Manuale.* Florence: Giunti O.S.

Zilcha-Mano, S., Keefe, J. R., Chui, H., Rubin, A., Barrett, M. S., & Barber, J. P. (2016). Reducing dropout in treatment for depression: Translating dropout predictors into individualized treatment recommendations. *Journal of Clinical Psychiatry*, 77, e1584-e1590. https://doi.org/10.4088/JCP.15m10081.

The invention claimed is:

1. A method for treating depression in a human subject, the method comprising:
    administering a fasting mimicking diet (FMD) component for a first time period, said fasting mimicking diet component providing less than 50% of the normal calorie intake of the subject with both protein restriction and sugar restriction; and
    administering a re-feeding diet component for a second time period, said re-feeding diet component providing 60-100% of the normal calorie intake of the subject;
    wherein the fasting mimicking diet component and the re-feeding diet component are administered for multiple cycles, and
    wherein said subject undergoes a psychotherapeutic treatment for the whole duration of said multiple cycles, wherein:
    the first time period is 5 days, and the second time period is 25-26 days;
    the multiple cycles comprise an administration once a month for at least 2 months;
    the fasting mimicking diet component provides the subject with 9 to 15 kcal/kg of body weight/day on day 1, and 6 to 10 kcal/kg of body weight/day for days 2 to 5; and
    the fasting mimicking diet component provides the subject with 100-1000 kcal/day.

2. The method according to claim 1, wherein said multiple cycles comprise an administration once a month for 3 months.

3. The method according to claim 1, wherein said fasting mimicking diet component provides the subject with a protein amount less than or equal to 36 g/day.

4. The method according to claim 1, wherein said fasting mimicking diet component comprises carbohydrates in such an amount as to provide no more than half of the calories provided by said diet component.

5. The method according to claim 1, wherein said fasting mimicking diet component provides the subject with no more than 11 kcal/kg of body weight/day.

6. The method according to claim 5, wherein said fasting mimicking diet component provides the subject with proteins in an amount that is no more than 0.4 g/kg of body weight/day.

7. The method according to claim 6, wherein said fasting mimicking diet component comprises proteins in an amount that is less than 15% of the total calories provided by the fasting mimicking diet component.

8. The method according to claim 4, wherein said fasting mimicking diet component comprises sugars in an amount that is less than 15% of the total calories provided by the fasting mimicking diet component.

9. The method according to claim 1, wherein said fasting mimicking diet component comprises at least 60% calories from fatty acids, 2-5% calories from glycerol and up to 5% calories from plant-based proteins and a maximum of 35% calories from carbohydrates.

10. The method according to claim 9, wherein said fasting mimicking diet component comprises complex carbohydrates from plant sources.

11. The method according to claim 10, wherein said complex carbohydrates are from soy or rice.

12. The method according to claim 9, wherein at least 50% of the calories from fatty acids are from coconut oil and tree nuts, selected from the group consisting of walnuts, macadamia nuts and almonds.

13. The method according to claim 1, wherein said normal calorie intake is 2000-3000 kcal/day for a male subject and 1600-2400 kcal/day for a female subject.

14. The method according to claim 1, wherein said psychotherapeutic treatment is functional therapy.

* * * * *